United States Patent [19]
Nestler et al.

[11] Patent Number: 4,617,408
[45] Date of Patent: Oct. 14, 1986

[54] MODIFIED TITANIUM (IV) ACETYLACETONATES

[75] Inventors: Heinz Nestler, Troisdorf-Eschmar; Dieter Barfurth, Troisdorf-Spich, both of Fed. Rep. of Germany

[73] Assignee: Dynamit Nobel AG, Cologne, Fed. Rep. of Germany

[21] Appl. No.: 713,302

[22] Filed: Mar. 18, 1985

[30] Foreign Application Priority Data

Jun. 30, 1984 [DE] Fed. Rep. of Germany ....... 3424189
Jul. 23, 1984 [DE] Fed. Rep. of Germany ....... 3427064

[51] Int. Cl.$^4$ .............................................. C07F 7/28
[52] U.S. Cl. .................................... 556/40; 502/152; 502/156; 106/300; 106/308 Q
[58] Field of Search .......................................... 556/40

[56] References Cited

U.S. PATENT DOCUMENTS

| 3,444,139 | 5/1969 | Jeurissen et al. | 556/40 |
| 3,694,475 | 9/1972 | Brook et al. | 556/40 |
| 3,856,839 | 12/1974 | Smith et al. | 556/40 |
| 4,438,039 | 3/1984 | Beers et al. | 556/40 |

*Primary Examiner*—Helen M. S. Sneed
*Attorney, Agent, or Firm*—Felfe & Lynch

[57] ABSTRACT

The present invention relates to new titanium chelates containing both acetylacetone and malonic acid dialkyl ester as chelating agents. The acetylacetone moiety is contained in these new chelates in amounts between 1.25 and 1.95 moles and the malonic acid dialkyl ester moiety in amounts between 0.05 and 0.75 moles per gram-atom of titanium. The new chelates have the same properties as the known titanium acetylacetonates; however, they have the advantage that they are only slightly yellow and in many applications they have an improved stability.

10 Claims, No Drawings

MODIFIED TITANIUM (IV) ACETYLACETONATES

BACKGROUND OF THE INVENTION

The subject matter of the present invention is dialkoxy titanium(IV)acetylacetonates which have the known typical properties of these chelated titanium compounds, but do not have the otherwise common red color.

It is known to use titanium chelates, especially dialkoxytitanium(IV)-bis-acetylacetonates, which are also referred to hereinafter as titanium acetylacetonates, as catalysts, crosslinking agents or coating materials, advantage being taken especially of the fact that their reactivity is lower than that of the tetraalkyl titanates, such as tetraisopropyltitanate for example, and of their reduced sensitivity to hydrolysis. This is important mainly in cases in which the intended catalytic or crosslinking action in a mixture of components is not to take place until a later moment in time, that is, after a period of standing. Practical examples of this can be considered to be flexographic printing inks on the basis of nitrocellulose, or slurries on the basis of titanium acetylacetonate for the production of fine casting molds; in any case, the hardening or crosslinking is not to take place in the container, which would undoubtedly happen with tetraalkyltitanates, but not until after the printing is performed, in the one case, or after the application of a coating to a model in the other.

Titanium acetylacetonates are commonly used in the form of an approximately 75% solution in the alcohol corresponding to the alkoxy groups of the chelate—usually isopropanol—directly as produced from one mole of tetraalkyltitanate and two moles of acetylacetone. The best-known representative of these titanium acetylacetonates is diisopropoxytitanium(IV)-bis-acetylacetonate.

These known titanium acetylacetonates are more or less red-colored due to circumstances of their manufacture. The intense red solution is usable for many applications (concentration by evaporation results in handling problems on account of orange-colored precipitates), but in other applications, such as the formulation of white or light-colored flexographic printing inks, the natural color is definitely undesirable.

The simple remedy of lowering the amount of acetylacetone to slightly less than two moles per gram-atom of titanium in the preparation of the titanium acetylacetonate, thus losing some of the stability of the chelate, but producing a yellow solution, does not give lasting results: after standing a while, the solution turns red again, and precipitation can occur. If the amount of acetylacetone is reduced excessively, say to 1.5 moles or less, titanate solutions are obtained which, although they are yellow, not red, their performance is much like that of the reactive and hydrolysis-sensitive tetraalkyltitanates.

The problem therefore was to find titanium chelates which would have the properties of the titanium acetylacetonates but would not be so strongly colored as these chelates are.

THE INVENTION

This problem has been solved by the invention of titanium acetylacetonates which are characterized by the fact that they contain, for each gram-atom of titanium, 0.05 to 0.75 moles of a malonic acid dialkyl ester moiety and [2-(0.05 to 0.75)] moles of the acetyl acetonate moiety bound to them. The new titanium chelates are furthermore described as the reaction product of one mole of tetraalkyltitanate with 1.25 to 1.95 moles of acetylacetone and 0.75 to 0.05 moles of malonic acid dialkyl ester, preferably with 1.5 to 1.75 moles of acetylacetone and 0.5 to 0.25 moles of malonic acid dialkyl ester, the sum of acetylacetone and malonic ester amounting to 2 moles with respect to 1 mole of tetralkyltitanate. The uppermost limit of the amount of acetylacetone is considered to be the level above which the reaction product is red-colored, while the lowermost claimed level is the chelate composition in which the technically important properties, such as reduced reactivity and compatibility with water, are still just perceptible.

The new titanium chelates are only slightly yellow and have the same low sensitivity to hydrolysis as the known titanium acetylacetonates, although degradation products of tetraalkyltitanates with 1 to 4 equivalents of malonic ester always give products or product mixtures which are just as sensitive to hydrolysis as the starting titanate itself. This means that malonic esters themselves are virtually ineffectual as complexing agents in the case of titanates.

The replacement of the acetylacetone moiety with the malonic acid alkyl ester moiety in accordance with the invention therefore has virtually no effect on the insensitivity to hydrolysis; on the other hand, the hydrolysis sensitivity of the reaction products of malonic acid alkyl esters with tetraalkyltitanate is substantially reduced by the partial replacement of the malonic acid alkyl ester with acetylacetone. It is therefore also possible, in accordance with the invention, to produce chelation in the reaction of titanium ester with malonic acid alkyl esters by replacing a portion of the malonic acid dialkyl ester with acetylacetone during preparation.

On account of the way in which they are produced, the new titanium chelates are in the form of solutions in the alcohol which corresponds to the alkyl moiety of the titanate used. Basically, it is possible to distill the alcohol and isolate the pure product. However, this isolation is not particularly advisable since the new chelates are used nearly always in dissolved form.

The tetraalkyl titanates used as starting compounds for the preparation of the new compounds can be any desired representatives of this group, chiefly $C_1$–$C_6$-alkyl titanate, and preferably isopropyl titanate and butyl titanate. In the new compounds, two moles of these alkoxy moieties per gram-atom of titanium always remain bound to the central titanium atom.

The term, malonic acid dialkyl esters, as used herein, is to be understood to refer to compounds of the formula $(ROOC)_2CR'_2$ or $(ROOC)_2C=CH-OR$ in which formulas, $R=C_1$ to $C_4$-alkyl and $R'=H$ or $C_1$ to $C_4$-alkyl, the alkyl groups being able to be identical or different. Examples of such compounds are: malonic acid diethylesters, malonic acid-di-butylester, butylmalonic acid dimethylester, ethoxymethylenemalonic acid diethylester.

The preparation of the claimed titanium chelates is performed quite simply by feeding the amounts of acetylacetone and malonic ester which are required for the reaction, into the tetraalkyltitanate placed in a suitable reaction vessel. Due to the reaction heat that develops the reaction mixture heats up to about 70° to 80° C. To complete the reaction the mixture is held at this temperature for about another half-hour, heating it additionally if necessary. The titanium chelate then forms in a solution of about 70 to 80% in the alcohol that is released by the reaction of the chelating agents with the starting titanate. The chelate solution can be used directly as is.

It is also possible to use as starting product solutions of the tetraalkyl-titanate in the alcohol corresponding to the alkoxy moiety. In this method of preparation more-dilute solutions of the new chelates are produced, which can also be used directly for many applications.

The titanium chelates of the invention can be used in all applications in which the known, commercial titanium acetylacetonate has been used heretofore. They have the advantage over the latter, however, of a substantially less intense coloration; also, they have a still better compatibility with water, so that undesired precipitation of titanium hydroxides is even more effectively prevented when water is present or formed in a reaction system.

EXAMPLE 1

Preparation of acetylacetone malonic acid diethylester-(1.75:0.25:1) titanium chelate from isopropyltitanate In a 1000-ml flask provided with stirrer, thermometer, dropping funnel and reflux condenser, 284 g (1 mole) of isopropyltitanate is placed, and a mixture of 175 g (1.75 moles) of acetylacetone (2,4-pentanedione) and 40 g (0.25 moles) of malonic acid diethyl ester is added through the dropping funnel such that the temperature of the reaction mixture does not rise above 75° C. When this addition is completed, the mixture is stirred for 30 minutes longer at 70° C.

The product is a light yellow, fluid liquid having the following characteristics:
Refractive index $n_D^{20}$: 1.4908
Viscosity (20° C.): 8.0 mPa.s
Titanium dioxide content: 16.0%
Solubility:
  (a) water in titanium chelate: max. 9.5 g water in 100 g titanium chelate
  (b) titanium chelate in water: max. 0.5 g titanium chelate in 100 grams of water.
  (c) in organic solvents:

| isopropanol: ethyl acetate: methyl ethyl ketone: heptane: toluene: methylene chloride: | 10% solution is clear and stable several months |
|---|---|

EXAMPLE 2

Preparation of acetylacetone-malonic acid diethylester-(1.50:0.50:1)-titanium chelate from isopropyltitanate In a 1000 ml flask provided with stirrer, thermometer, dropping funnel and reflux condenser, 284 g (1 mole) of isopropyltitanate is placed, and a mixture of 150 g (1.50 moles) of acetylacetone (2,4-pentanedione) and 80 g (0.50 moles) of malonic acid diethyl ester is added through the dropping funnel such that the temperature of the reaction mixture does not rise above 75° C. After this addition is completed, the mixture is stirred for another 30 minutes at 70° C. A yellow, fluid liquid is obtained having the following characteristics:

Refractive index $n_D^{20}$: 1.4835
Viscosity (20° C.): 8.5 mPa.s
Titanium dioxide content: 15.6%
Solubility:
  (a) Water in titanium chelate: max. 90 g of water in 100 g of titanium chelate
  (b) Titanium chelate in water: max. 0.5 g of titanium chelate in 100 g water
  (c) In organic solvents:

| isopropanol: ethyl acetate: methyl ethyl ketone: heptane: toluene: methylene chloride: | 10% solution clear and stable for several months |
|---|---|

EXAMPLE 3

Preparation of acetylacetone-malonic acid diethyl ester-(1.25:0.75:1)-titanium chelate from isopropyltitanate In a 1000-ml flask provided with stirrer, thermometer, dropping funnel and reflux condenser, 284 g (1 mole) of isopropyltitanate is placed and a mixture of 125 g (1.25 moles) of acetylacetone (2,4-pentanedione) and 120 g (0.75 moles) of malonic acid diethyl ester is added through the dropping funnel such that the temperature of the reaction mixture did not rise above 75° C. After the addition is completed, the mixture is stirred for another 30 minutes at 70° C. A yellow, fluid liquid is obtained having the following characteristics:
Refractive index $n_D^{20}$: 1.4785
Viscosity (20° C.): 7.5 mPa.s
Titanium dioxide content: 15.1%
Solubility:
  (a) water in titanium chelate: max. 60 g water in 100 g of titanium chelate
  (b) titanium chelate in water: max 0.5 g titanium chelate in 100 g water
  (c) in organic solvents:

| isopropanol: ethyl acetate: methyl ethyl ketone: heptane: toluene: methylene chloride: | 10% solution clear and stable for several months |
|---|---|

EXAMPLE 4

Determining the reactivity of the new titanium chelates, prepared in accordance with Examples 1 to 3, with nitrocellulose solutions The usefulness of a titanium chelate for application as an additive for flexographic printing inks can be determined by a simple test with a nitrocellulose solution, the procedure being, as a rule, to add to the nitrocellulose solution different percentages of the titanium chelate to be tested, and observing the effect thereof, e.g., thickening and gelling of the nitrocellulose solution. In the following table are listed the results of such testing with the titanium chelates prepared per Examples 1 to 3.

| Titanium chelate added | Addition of 1 ml of titanium chelate to 10 ml of a 10% nitrocellulose solution of type | |
|---|---|---|
| | Norm 30 A (soluble in alcohol) | Norm 34 E (soluble in ester) |
| (a) Titanium acetylacetonate (standard product for comparison) | no change | no change |
| (b) Titanium chelate of Example 1 | no change | no change |
| (c) Titanium chelate of Example 2 | slight thickening | no change |
| (d) Titanium chelate of Example 3 | moderate thickening | no change |
| (e) acetylacetone-malonic acid diethyl ester-(1:1:1)-titanium chelate | gels in 24 h | no change |
| (f) acetylacetone-(1.5:1) titanium chelate | gels immediately | moderate thickening |

Examples (a), (e) and (f) serve for purposes of comparison. All of the products were prepared in a manner similar to the one described in Example 1; only the ratio of acetyl acetone to titanic acid ester was changed. It amounted in Example (a) to 2:1, in Example (f) to 1.5:1, and in Example (e) to 1:1, one mole of malonic acid diethyl ester being additionally used.

The nitrocellulose types listed in the table are widely used as standard binding agents in the printing ink industry. In the case of type 30 A, additives which produce no more than a moderate thickening are considered usable.

EXAMPLE 5

Description of the adhesion-improving action of an addition of the new titanium chelate of Example 2 in a nitrocellulose printing ink 2% of the titanium chelate of the invention prepared in accordance with Example 2 was added to a nitrocellulose printing ink containing 25% nitrocellulose of Norm type 34 E, dissolved in ethanol-ethylacetate, and titanium dioxide as white pigment, and the mixture was stirred for a few minutes. By means of a film drawing spiral the printing ink thus modified was applied to a polypropylene film previously treated with a corona, in a wet coating thickness of 12 microns, and after 60 minutes of air drying it was dried for 10 minutes at 60° C. in a convection drying oven. Then the adhesion of the printing ink to the polypropylene was determined by pulling off a piece of adhesive tape as follows: a pressure-sensitive film strip (e.g., Tesafilm) was attached on an area of about 4 sq.cm. and pulled off again with a jerk. In this test, 0 to 10% of the printing ink was pulled from the substrate. For comparison, the percentage pulled off in the case of the addition of 2% of commercial titanium acetylacetonate to the printing ink was 15 to 25%.

It will be understood that the specification and examples are illustrative but not limitative of the present invention and that other embodiments within the spirit and scope of the invention will suggest themselves to those skilled in the art.

EXAMPLE 6

Preparation of acetylacetone butyl malonic acid diethylester-(1.75:0.25:1)titanium chelate from isopropyltitanate In a 1000-ml flask provided with stirrer, thermometer, dropping funnel and reflux condenser, 284 g (1 mole) of isopropyltitanate is placed, and a mixture of 175 g (1.75 moles) of acetylacetone (2,4-pentanedione) and 54 g (0.25 moles) of butyl malonic acid diethyl ester is added through the dropping funnel such that the temperature of the reaction mixture does not rise above 75° C. When this addition is completed, the mixture is stirred for further 30 minutes at 70° C.

The product is a light yellow, fluid liquid having the following characteristics:
Refractive index $n_D^{20}$: 1.4897
Viscosity (20° C.): 9.3 mPa.s
Titanium dioxide content: 15.6%
Solubility:
  (a) water in titanium chelate: max. 35 g water in 100 g titanium chelate
  (b) titanium chelate in water: max. 0,5 g titanium chelate in 100 grams of water
  (c) in organic solvents:

| | |
|---|---|
| isopropanol: ethyl acetate: methyl ethyl ketone: heptane: toluene: methylene chloride: | 10% solution is clear and stable several months |

EXAMPLE 7

Preparation of acetylacetone-ethoxy methylene malonic acid diethylester-(1.75:0.25:1) titanium chelate from isopropyltitanate.

In a 1000-ml flask provided with stirrer, thermometer, dropping funnel and reflux condenser, 284 g (1 mole) of isopropyltitanate is placed, and a mixture of 175 g (1.75 moles) of acetylacetone (2,4-pentanedione) and 54 g (0.25 moles) of ethoxy methylene malonic acid diethyl ester is added through the dropping funnel such that the temperature of the reaction mixture does not rise above 75° C. When this addition is completed, the mixture is stirred for further 30 minutes at 70° C.

The product is a light yellow, fluid liquid having the following characteristics:
Refractive index $n_D^{20}$: 1.4943
Viscosity (20° C.): 12,0 mPa.s
Titanium dioxide content: 15.6%
Solubility:
  (a) water in titanium chelate: max. 35 g water in 100 g titanium chelate
  (b) titanium chelate in water: max. 0,5 g titanium chelate in 100 grams of water
  (c) in organic solvents:

| | |
|---|---|
| isopropanol: ethyl acetate: methyl ethyl ketone: heptane: toluene: methylene chloride: | 10% solution is clear and stable several months |

We claim:

1. A dialkoxy titanium (IV) acetylacetonate chelate containing 0.05 to 0.75 moles of a malonic acid dialkyl ester moiety per gram-atom of titanium, the malonic acid dialkyl ester moiety being of the formulas ROOC—CR'R'—COOR, or (ROOC)$_2$C=CH—OR wherein R represents alike or different alkyl moieties of 1 to 4 carbon atoms, and R' represents H or R.

2. The chelate of claim 1, wherein R is ethyl.

3. A method of preparing the dialkoxy titanium(IV)acetylacetonates of claim 1, comprising reacting a tetraalkyltitanate with so much acetylacetone and malonic acid dialkyl esters of the formula ROOC—CR'—CR'—COOR, wherein R represents the same or different alkyl moieties of 1 to 4 carbon atoms and R' represents H or R, that, for each gram-atom of titanium, 1.25 to 1.95 moles of acetyl acetone and 0.75 to 0.05 moles of malonic acid dialkyl ester are used, and the sum of the number of moles of acetylacetone and the number of moles of malonic acid dialkyl ester amounts to 2 moles per gram-atom of titanium.

4. The method of claim 3, wherein R is ethyl.

5. The method of claim 3 wherein 1.5 to 1.75 moles of acetyl acetone are used for each gram-atom of titanium.

6. The method of claim 3 wherein 0.5 to 0.25 moles of malonic acid and dialkyl ester are used for each gram-atom of titanium.

7. The method of claim 5 wherein 0.5 to 0.25 moles of malonic acid dialkyl ester are used for each gram-atom of titanium.

8. The method of claim 5 wherein R is ethyl.

9. The method of claim 6 wherein R is ethyl.

10. The method of claim 7 wherein R is ethyl.

* * * * *

UNITED STATES PATENT AND TRADEMARK OFFICE
CERTIFICATE OF CORRECTION

PATENT NO. : 4,617,408

DATED : October 14, 1986

INVENTOR(S) : Heinz Nestler et al

It is certified that error appears in the above-identified patent and that said Letters Patent is hereby corrected as shown below:

Column 3, line 41, "9.5 g" should read --95 g--.

Column 3, line 62, "acetylacetonate" should read --acetylacetone--.

The paragraph appearing at column 5, lines 64 to 68 of the patent should appear in column 6, penultimate line (above "We claim").

Column 8, line 9, "malonic acid and dialkyl ester" should read --malonic acid dialkyl ester--.

Signed and Sealed this

Twenty-seventh Day of November, 1990

Attest:

HARRY F. MANBECK, JR.

Attesting Officer

Commissioner of Patents and Trademarks